United States Patent
Nasar

(10) Patent No.: US 10,531,902 B2
(45) Date of Patent: Jan. 14, 2020

(54) COMBINED TENSIONING AND SCREWDRIVER DEVICE FOR PERCUTANEOUS SURGERY

(71) Applicant: Alan Nasar, Freehold, NJ (US)

(72) Inventor: Alan Nasar, Freehold, NJ (US)

( * ) Notice: Subject to any disclaimer, the term of this patent is extended or adjusted under 35 U.S.C. 154(b) by 154 days.

(21) Appl. No.: 15/646,802

(22) Filed: Jul. 11, 2017

(65) Prior Publication Data

US 2019/0015141 A1     Jan. 17, 2019

(51) Int. Cl.
*A61B 17/82* (2006.01)
*A61B 17/88* (2006.01)

(52) U.S. Cl.
CPC .......... *A61B 17/82* (2013.01); *A61B 17/8861* (2013.01)

(58) Field of Classification Search
CPC .............................. A61B 17/82; A61B 17/8861
See application file for complete search history.

(56) References Cited

U.S. PATENT DOCUMENTS 2,943,650 A * 7/1960 Rubin ................ A61B 17/8861
140/119
5,116,340 A * 5/1992 Songer ............... A61B 17/8861
29/282
5,312,410 A * 5/1994 Miller ................ A61B 17/8861
606/103
5,772,663 A * 6/1998 Whiteside .............. A61B 17/82
606/103

* cited by examiner

*Primary Examiner* — David W Bates

(57) ABSTRACT

A method and apparatus is provided for conducting percutaneous surgery using a cable passer device 200, a crimping device 100, a screwdriver device 120, a cable tensioning device 130, and a cutting device 300. The percutaneous cable passer device 200 is for inserting into an incision during percutaneous surgery having a cable 110 for making a loop around the bone. The crimping device 100 is for threading the tip of the cable 110 through an opening in crimping device 100. The cannulated screwdriver device 120 has a tip 126 for threading the tip of the cable 110 through the tip 126, and an exit port 124 for pulling the cable 110 while pushing said screwdriver device 120 towards the bone. The cable tensioning device 130 has an internal passage way 132 for threading the tip of the cable 110 through it. The screwdriver device 120 is rotatable while holding the cable tensioning device 130, thus deploying the crimping device 100. The cable cutting device 140 has a tip for threading the cable 110 through the tip of the cable cutting device 300 for cutting the cable 110 when it is touching the crimping device 100.

1 Claim, 6 Drawing Sheets

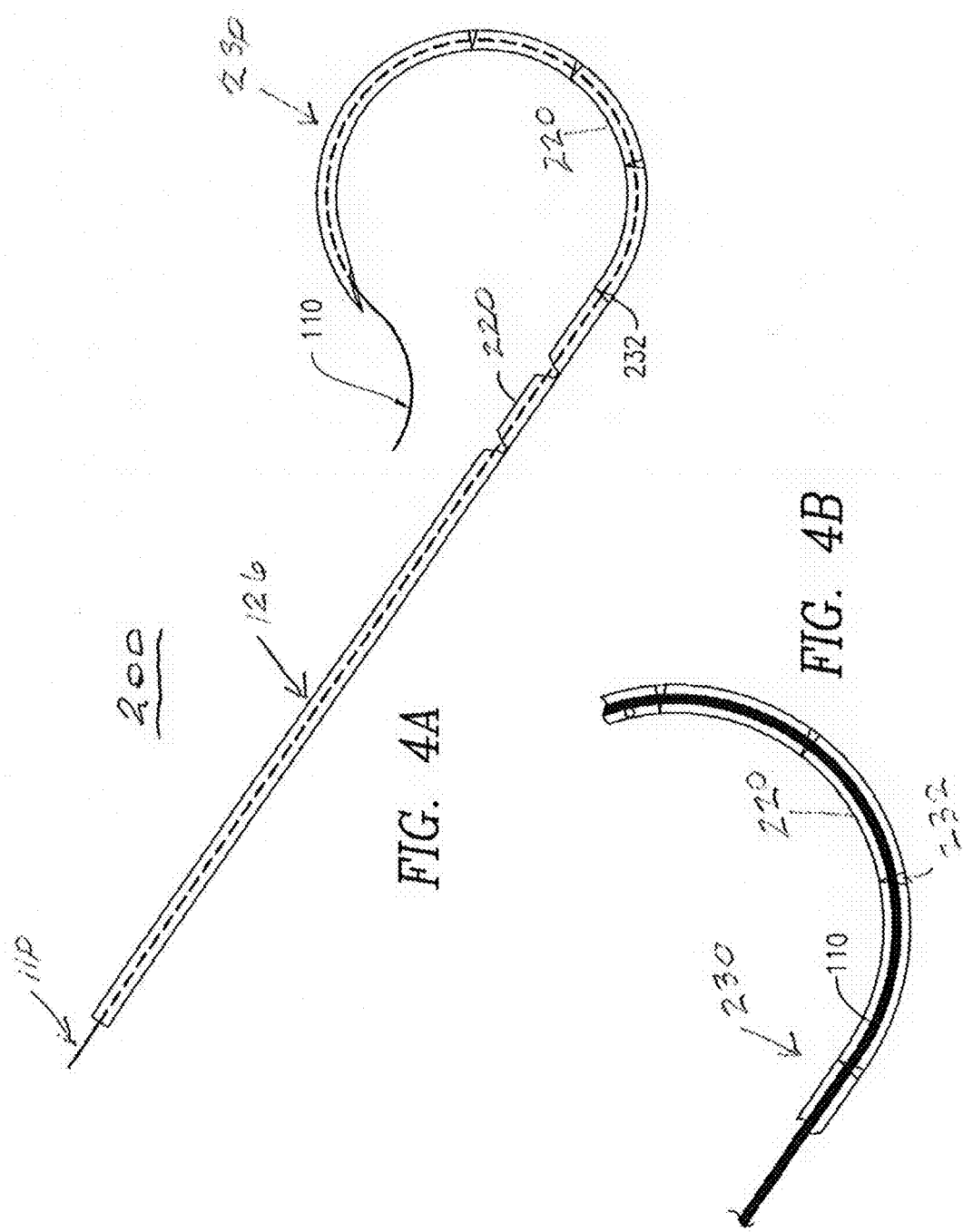

COMBINED TENSIONING AND SCREWDRIVER DEVICE FOR PERCUTANEOUS SURGERY

FIELD OF THE INVENTION

The present invention relates to the field of percutaneous surgery involving a combined tensioning and screwdriver device, and a cerclage cable passer device, which is constructed to more easily encircle the bone.

BACKGROUND OF THE INVENTION

The prior art discloses separate tensioning devices and surgical screwdriver devices, but they have drawbacks which are overcome by the present invention. In addition, the cerclage cable passer device is provided with a unique structure to more easily encircle the bone. Further, the cable cutter of the present invention has a unique structure to more easily and accurately cut the cable.

DESCRIPTION OF THE PRIOR ART

The prior art discloses separate tensioning devices and surgical screwdriver devices, but they have drawbacks which are overcome by the present invention. In addition, the prior art does not disclose a cerclage cable passer device having a unique structure to more easily encircle the bone. Further, the prior art does not disclose a cable cutter structure to more easily and accurately cut the cable.

OBJECTS OF THE INVENTION

It is an object of the present invention to provide a combined screwdriver device and tensioning device for percutaneous surgery, wherein the tensioning device does not enter the incision.

It is another object of the present invention to provide a screwdriver device which can be seated on the bone without direct visualization.

It is another object of the present invention to provide minimally invasive surgery.

It is another object of the present invention to provide a cerclage passer device which is constructed to be inserted around the bone through one small incision, wherein the cable passer is structured to more easily encircle the bone.

SUMMARY OF THE INVENTION

A method and apparatus is provided for conducting percutaneous surgery using a cable passer device 200, a crimping device 100, a screwdriver device 120, a cable tensioning device 130, and a cutting device 300. The percutaneous cable passer device 200 is for inserting into an incision during percutaneous surgery having a cable 110 for making a loop around the bone. The crimping device 100 is for threading the tip of the cable 110 through an opening in crimping device 100. The cannulated screwdriver device 120 has a tip 126 for threading the tip of the cable 110 through the tip 126, and an exit port 124 for pulling the cable 110 while pushing said screwdriver device 120 towards the bone. The cable tensioning device 130 has an internal passage way 132 for threading the tip of the cable 110 through it. The screwdriver device 120 is rotatable while holding the cable tensioning device 130, thus deploying the crimping device 100. The cable cutting device 300 has a tip for threading the cable 110 through the tip of the cable cutting device 300 for cutting the cable 110 when it is touching the crimping device 100.

BRIEF DESCRIPTION OF THE DRAWINGS

FIG. 4A shows another view of the cable passer 200 having segments 220;

FIG. 4B shows a partial view of the cable passer 200 having segments 220;

DETAILED DESCRIPTION OF THE PREFERRED EMBODIMENT

Figure 1:
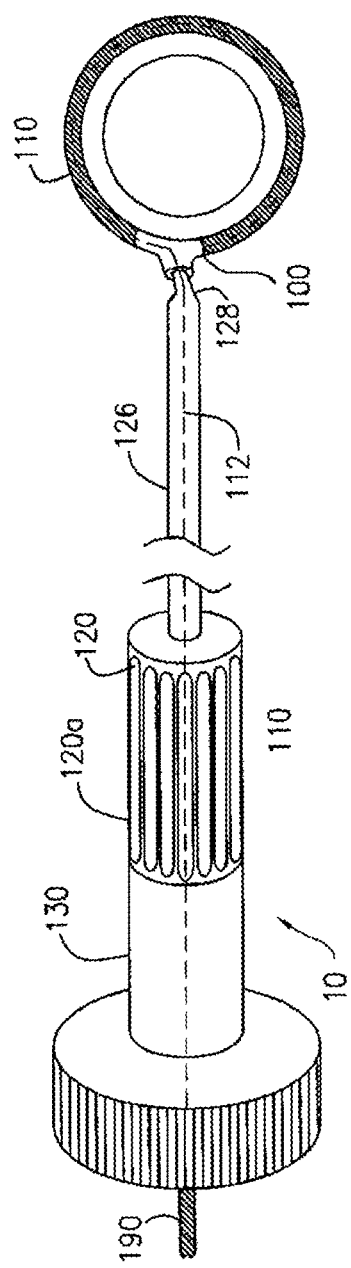
FIG. 1 is a longitudinal view of the combined tensioning device 130, the cannulated screwdriver 120, and the crimping device 100.
Figure 2:
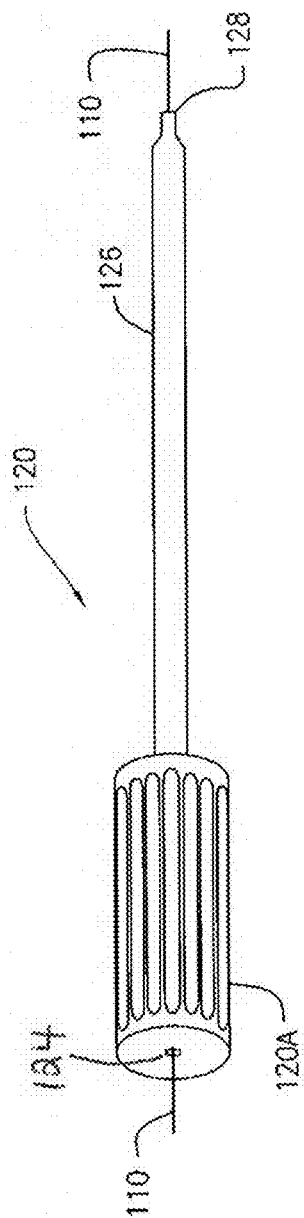
FIG. 2 is a longitudinal view of the cannulated screwdriver device 120 with cable 110 extending through it.

In the combined tensioner and screwdriver tool of the present invention, shown in FIG. 1, includes tensioning device 130 which is integrated with the cannulated screwdriver device 120, which is integrated with crimping device 100 to form a single integral unit, which provides the advantages described below. This structure avoids having separate devices, as in the prior art, which use a separate crimping device, a separate tensioning device, and a separate screwdriver device.

The combined tool 10 of the present invention provides significant improvements by having the cable 110 pass from the tensioning device 130 and through the screwdriver device 120 to the tensioning device 130. When doing surgery, the difficulty is often getting the tools to interact with the device while it is inserted inside the body. Typically, there is muscle and bloody fluid impeding access and visualization.

The second advantage is the less devices that need to be introduced into the body, and the less directions that the devices need to be introduced to, results in minimizing of the surgical work. This invention only uses one single combined device or tool that is placed into the body in contact with the cable and crimp, which is the cannulated screwdriver device 120. The tensioning device 130 is placed in line with the screwdriver device 120 and is integrated with it, as shown in FIG. 1. Accordingly, the tensioning device 130 never needs to enter the body.

The third advantage is that the cable 110 actually guides the screwdriver device 120 into the crimping device 100. Thus, the end of screwdriver device 120 can be seated on the bone and deployed, which can be done without direct visualization. This is especially suited for minimally invasive surgery and can be used in a fluoroscopy guided technique. This invention is well suited towards minimally invasive surgery as the exposure needed to deploy and tension the cable 110 is less than current methods, since there is less access to the cable 110 and a crimp is provided by use of the cannulated screwdriver device 120 that also acts with the tensioning device 130.

In the present invention, as shown in FIG. 1, the cable 110 passes through tensioning device 130 and then passes through a center passageway 122 formed in the screwdriver device 120 and at the tip 124, the cable passes out the back end of the cannulated screwdriver 120, where it is tensioned. In the prior art, the cable exits separately and moves in another direction from where the screwdriver is placed. There are two advantages to having the cable 110 travel through the screwdriver device 120. First, the tensioning device 130 does not need to be brought into the wound and next to the patient so it is ease-of-use. Secondly, the doctor only has to deal with one access direction not a second access direction. The cable 110 then passes around crimping device 100 to encircle the bone, as shown in FIG. 1.

The surgical steps for percutaneous cable insertion, tensioning, crimping, and cutting are performed using a percutaneous cable 110 with crimping device 100, a percutaneous cable inserter 106, a cannulated screwdriver device 120, a tensioning device 130, and a percutaneous cutting device 300 include the following sequence of steps:

1) Identify the area of bone to be cabled, perform a reduction maneuver as necessary, place a fixation device, such as plate, strut, or rod in and/or around the bone as necessary, and use imaging such as fluoroscopy as necessary to guide subsequent steps.
2) Make a stab incision over the site to be cabled. The incision size should be just enough to accommodate percutaneous instruments.
3) Dissect from skin to bone using a cannula with a sharp obturator or sharp cannula.
4) Insert the percutaneous cable passer 200 through the incision and verify that it is in appropriate position.
5) Deploy the percutaneous cable passer 200 and pass the cable 110 around the bone and back out of the incision site making a loop 112 around the bone.
6) Thread the tip of the cable 110 through the opening 102 in the crimping device 100.
7) Pull the tip of the cable 110 away from the bone by sliding the crimping device 100 down the cable 110 toward the bone.
8) Thread the tip of the cable 110 through the shaft 126 and tip 128 of the cannulated screwdriver device 120.
9) Seat the tip of the screwdriver device 120 on the bone.
10) Pull the cable 110 as it exits the back of the cannulated screwdriver device 120 while pushing the screwdriver 120 towards the bone. This will push the crimp down to the bone and take out the slack in the cable 110 and manually tension the cable 110. Verify that the position of the cable 110 is correct.
11) Thread the tip 112 of the cable 110 through the cable tensioning device 130 and through the screwdriver device 120, which are connected together.
12) Tension the cable 110 to the appropriate tension using the cable tensioning device 130.
13) Rotate the screwdriver device 120 using handle 120a while holding the cable tensioning device 130, thus deploying the crimping device 100 to crimp the cable 110.
14) Release the cable tensioning device 130 and pull it off the cable 110 and out of the body.
15) Then, pull the screwdriver device 120 off the cable 110.
16) Thread the cable 110 through the tip of the cable cutting device 300.
17) Pull the cable tip out the back of the cable cutting device 300 while pushing the cutting device towards the crimping device 100 to cut off the excess cable 110.
18) Once the cable cutting device 300 is touching the crimp, deploy the cutting device 300 to cut the cable 110.
19) Remove the cut end of the cable 110 and the cutting device 300 from the incision.
20) Close the skin with customary surgical technique.

Second Embodiment

Cerclage Cable Passer 200

Figure 3:
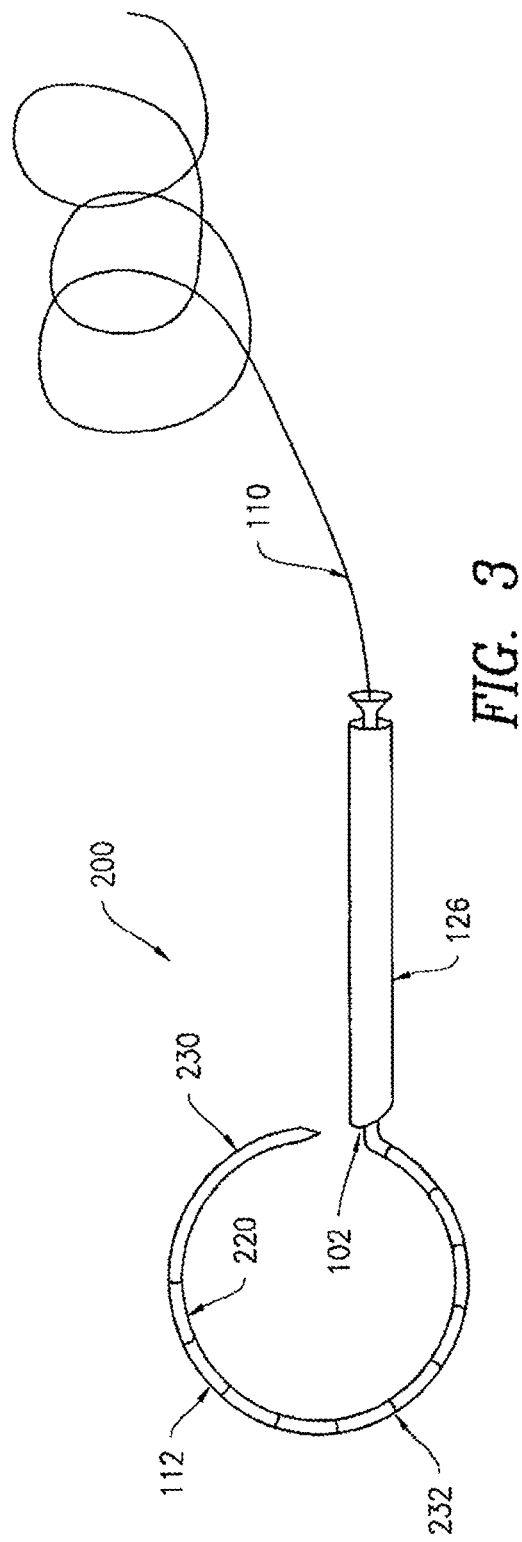
FIG. 3 is a front view of the cerclage cable passer 200.
Figure 3A:
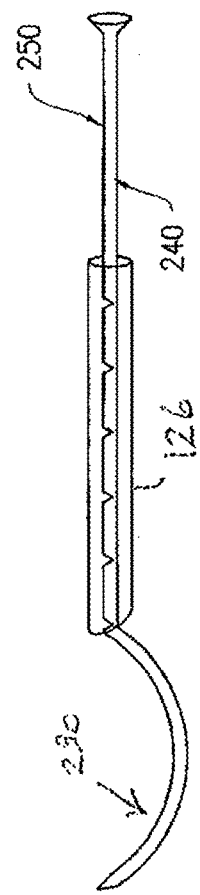
FIG. 3A is an interior view of the cerclage cable passer 200.
Figure 4:
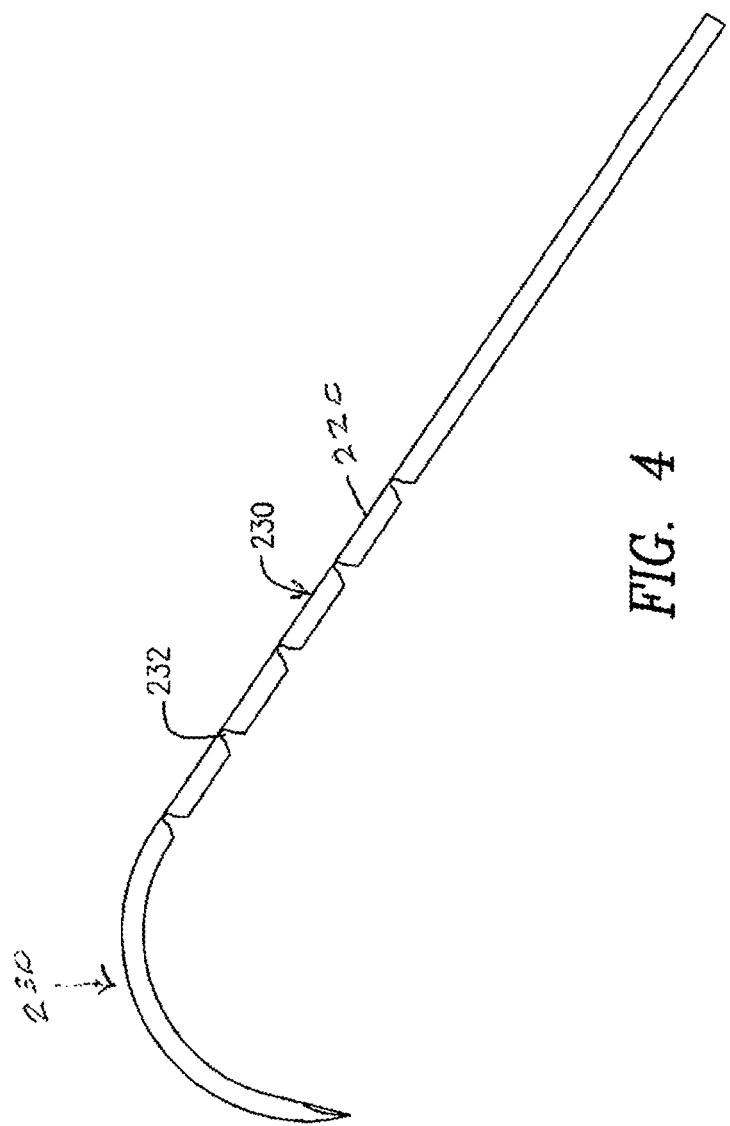
FIG. 4 shows details of the hinges 232 in cable passer, which forms a curved configuration to encircle the bone.

The principles parts of the cerclage cable passer 200 are shown in FIGS. 3 and 4 as follows: a curved tip 210 having multiple segments 220 are attached to the curved tip 260. All of the components are cannulated (that is hollow). The segments 220 of the cable 230 are hinged as shown at hinge points 232, and are connected to each other in such a way that when tension is applied to the flexion cable 230, the cable passer 200 will be easily pulled into a circular configuration. This type of construction is novel and makes it easy for the cable 230 to encircle the bone. When the cable passer 200 is housed in the cannula 240, it assumes a straight position.

In operation, the inserter 250 is placed into the body through a percutaneous incision in a straight configuration while it is in the cannula 240. Once the tip 210 starts to curve around the bone, the cannula 240 is incrementally withdrawn as the inserter 250 is advanced, with the hinges 232 constructed so as to cause the cable 230 to more easily encircle the bone. The tension on the flexion cable 230 acts to curl or curve the inserter 250 around the bone as it is advanced. Once it is sufficiently advanced to wrap around the bone, a guide wire 260 can be placed through the cable passer 200 and retrieved from the same incision. The guide wire 260 attaches to the cerclage cable 230, which is then pulled around the bone through the same incision. The end result is that the cerclage cable 230 is passed around the bone with use of the percutaneous cable passer 200 through one small incision and without the need for dissection and exposure of deep tissue, such as fascia, muscle, tendon, and bone. This is a minimally invasive technique.

Third Embodiment

Cable Cutter 300

Figure 5:
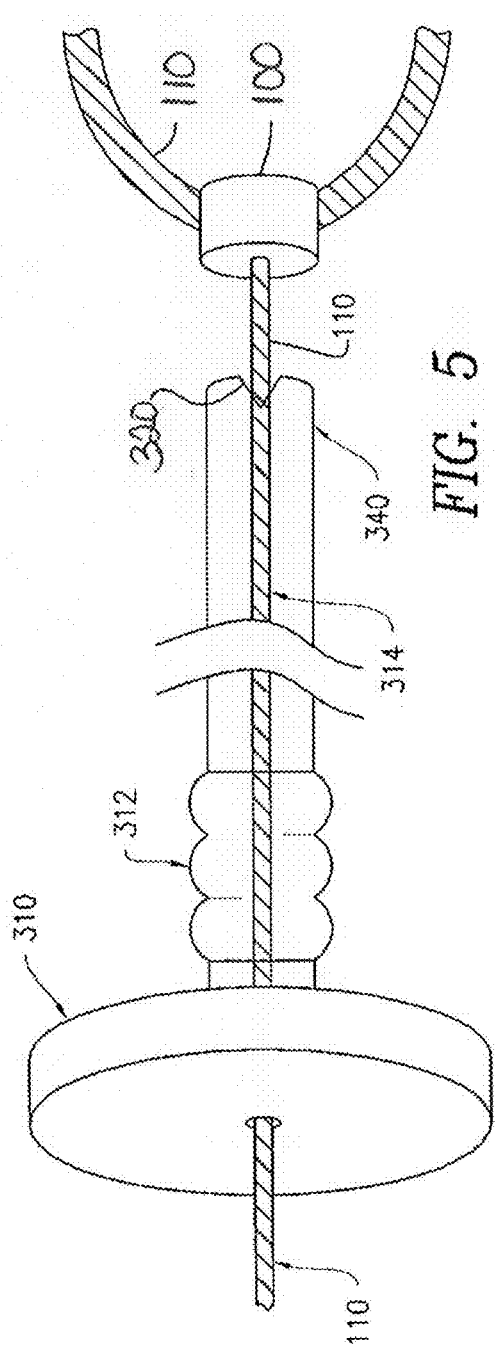
FIG. 5 is a cross sectional view of the cable cutter 300.
Figure 5A:
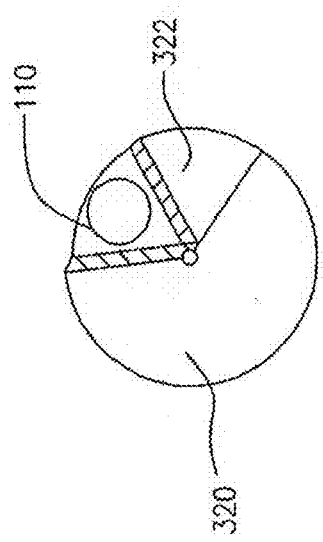
FIG. 5A is a cross sectional view of FIG. 5 showing the cutter blade 322 for cutting the cable 110.

The principal parts of the new cable cutter 300 are shown in FIGS. 5 and 5A and include a rotating handle 310 having a gripping section 312 and a central passageway 314 to receiving there through the cable 110. A cutting blade 320 is shown at the end of the rotating handle 310 for cutting the cable 110. The cable 110 is shown entering the skin layer 330 at the wound sight 332.

FIG. 5A shows a cross sectional view of the blade 320 attached to the outer cannula 340, which has an inner blade 322 for cutting the cable 110. In operation, the handle 310 is rotated to cut the cable 110 between the two blades 320 and 322.

This unique cable cutter 300 provides a new structure to more easily and accurately cut the cable 110 using the rotating blades.

Advantages of the Present Invention

It is an advantage of the present invention to provide a combined screwdriver device and tensioning device for percutaneous surgery, wherein the tensioning device does not enter the incision.

It is another advantage of the present invention to provide a screwdriver device which can be seated on the bone without direct visualization.

It is another advantage of the present invention to provide minimally invasive surgery.

It is another advantage of the present invention to provide a cerclage passer device which is inserted around the bone through one small incision.

A latitude of modification, change and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

What is claimed is:

1. An apparatus for conducting percutaneous surgery on a bone using a cable (110), the apparatus having a cable passer (200), the cable (110), a crimping device (100), a cannulated screwdriver device (120), a cable tensioning device (130), and a cutting device (300), wherein:
    a) said percutaneous cable passer (200) has multiple hollow segments (220) that are hingedly connected to each other and the cable passer (200) has a curved tip (230) attached to one of the hollow segments (220) for inserting said cable (110) into an incision during percutaneous surgery and causing the cable (110) to encircle the bone;
    b) the crimping device (100) is attached to said cable (110), the crimping device (100) including an opening for threading a tip of the cable (110) through the opening in said crimping device (100);
    c) said opening in the crimping device (100) is configured for moving the crimping device (100) along the cable (110) toward the bone when the cable is encircling the bone;
    d) said cannulated screwdriver device (120) including a tip (128) for threading the tip of the cable (110) through the tip (122) of said cannulated screwdriver (120), and said cable tensioning device (130) is coupled with said screwdriver device (120) to apply tension to the cable (110) by applying pulling force on said cable (110) to cause the cable which has encircled the bone to compress the bone, said cannulated screwdriver (120) having an exit port (128) for permitting the tensioning device (130) to pull the cable (110) while said screwdriver device (120) is being pushed towards said crimping device (100) to take out slack in the cable and to permit manually tensioning the cable (110), said tensioning device (130) being configured to be compressed to said screwdriver (120) when the screwdriver is coupled to said crimping device (100) so that said cable (110) exits said crimping device (100) and travels through said screwdriver (120), and through said exit port (128);
    e) said screwdriver device (120) is rotatable while holding said cable tensioning device (130), such rotation deploying said crimping device (100) by causing the crimping device (100) to be crimped onto the cable (110);
    f) said cable tensioning device (130) and said screwdriver (120) are removable from the cable (110);
    g) said cable cutting device (300) includes a rotating handle (310) and a central passage way (314) for receiving said cable (110), said cutting device having a tip (320) for threading the cable 110 through the tip (320) of said cable cutting device (300); and
    h) said cable cutting device (300) is configured for cutting the cable (110) when the cutting device (300) is touching said crimping device (100).

* * * * *